United States Patent

Massonne et al.

[11] Patent Number: 6,147,227
[45] Date of Patent: Nov. 14, 2000

[54] PROCESS FOR PREPARING PHTHALIDES

[75] Inventors: Klemens Massonne, Westheim; Rainer Becker, Bad Dürkheim; Horst Neuhauser, Dudenhofen; Horst Zimmermann, Mannheim; Wolfgang Reif, Frankenthal, all of Germany; Peter Cramers, Bubendorf; Daniel Nardin, Horriwil, both of Switzerland

[73] Assignee: BASF Aktiengesellschaft, Ludwigshafen, Germany

[21] Appl. No.: 09/269,773

[22] PCT Filed: Sep. 22, 1997

[86] PCT No.: PCT/EP97/05186

§ 371 Date: Apr. 1, 1999

§ 102(e) Date: Apr. 1, 1999

[87] PCT Pub. No.: WO98/14441

PCT Pub. Date: Apr. 9, 1998

[30] Foreign Application Priority Data

Oct. 1, 1996 [DE] Germany .......................... 196 40 554

[51] Int. Cl.[7] .................................................. C07D 307/88
[52] U.S. Cl. ........................................................ 549/307
[58] Field of Search ............................................ 549/307

[56] References Cited

U.S. PATENT DOCUMENTS

| | | | |
|---|---|---|---|
| 2,114,696 | 4/1938 | Austin et al. ........................... | 260/123 |
| 4,485,246 | 11/1984 | Lyons ..................................... | 549/302 |
| 4,528,385 | 7/1985 | ausderFuenten et al. .............. | 549/307 |
| 5,296,614 | 3/1994 | Henkelmann et al. ................. | 549/307 |

FOREIGN PATENT DOCUMENTS

| | | |
|---|---|---|
| 089417 | 9/1983 | European Pat. Off. . |
| 542037 | 5/1993 | European Pat. Off. . |

OTHER PUBLICATIONS

Houben–Weyl, Methoden der organischen Chemie, 6/2, 1963, pp. 732–733 (along with English translation).

*Primary Examiner*—Bernard Dentz
*Attorney, Agent, or Firm*—Keil & Weinkauf

[57] ABSTRACT

A process for preparing phthalides of the general formula I,

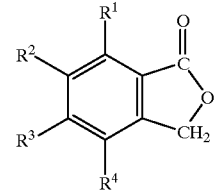

where $R^1$, $R^2$, $R^3$ and $R^4$ are independently hydrogen, $C_1$–$C_4$-alkyl or $C_1$–$C_4$-alkoxy, by hydrogenating phthalic anhydrides of the general formula II,

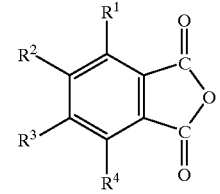

where $R^1$, $R^2$, $R^3$ and $R^4$ are each as defined above, with hydrogen in the presence of suspended catalysts of the Raney type in a hydrogenation apparatus by using a mixing apparatus to mix a liquid phase, which includes the catalyst and the phthalic anhydride used and resulting phthalide, and a gas phase, which includes the hydrogenating hydrogen, comprises using the mixing apparatus to introduce a mixing intensity of at least 50 W/l into the liquid phase.

5 Claims, No Drawings

PROCESS FOR PREPARING PHTHALIDES

This application claims priority under 35 U.S.C. 371 from PCT/EP97/05186 filed Sep. 22, 1997.

DESCRIPTION

The present invention relates to a process for preparing phthalides by catalytic hydrogenation of phthalic anhydrides with the aid of suspended Raney catalysts.

DE-C-28 03 319 discloses preparing phthalide by catalytic hydrogenation of phthalic anhydride in the gas phase using copper and aluminum catalysts. However, this process is prohibitively costly in the product isolation stage, involving as it does multistage condensation and a downstream waste gas scrub.

U.S. Pat. No. 4,485,246 discloses preparing phthalide from phthalic anhydride by hydrogenation using homogeneous ruthenium catalysts. Catalyst recovery is difficult in these processes.

EP-A-542 037 discloses a process for preparing phthalides by catalytic hydrogenation of phthalic anhydride over fixed bed catalysts in tubular reactors or tube bundle reactors or suspended catalysts in a stirred autoclave. If batch operated, said process requires large amounts of catalyst and long hydrogenation times. Continuous operation requires high pressures to obtain complete conversion.

EP-B-89 417 describes the catalytic hydrogenation of phthalic anhydride to phthalide with the aid of a nickel catalyst immobilized on a support material using autoclaves with lift stirrer and methyl benzoate as mandatory solvent. The process has the disadvantage of high catalyst requirements and long reaction times.

Houben/Weyl, Methoden der organischen Chemie, 6/2 (1963), pages 732 to 733, and also U.S. Pat. No. 2,114,696 describe the hydrogenation of phthalic anhydride to phthalide with the aid of Raney nickel catalyst in a shaking autoclave, but a hydrogen pressure of 165 bar and ethanol as solvent affords a phthalide yield of only 73%.

It is an object of the present invention to remedy the aforementioned disadvantages of existing processes for the catalytic hydrogenation of phthalic anhydrides.

We have found that this object is achieved by a novel and improved process for preparing phthalides of the general formula I,

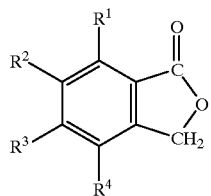

where $R^1$, $R^2$, $R^3$ and $R^4$ are independently hydrogen, $C_1$–$C_4$-alkyl or $C_1$–$C_4$-alkoxy, by hydrogenating phthalic anhydrides of the general formula II,

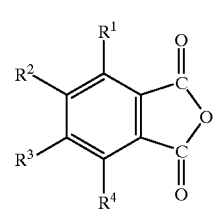

where $R^1$, $R^2$, $R^3$ and $R^4$ are each as defined above, with hydrogen in the presence of suspended catalysts of the Raney type in a hydrogenation apparatus by using a mixing apparatus to mix a liquid phase, which includes the catalyst and the phthalic anhydride used and resulting phthalide, and a gas phase, which includes the hydrogenating hydrogen, which comprises using the mixing apparatus to introduce a mixing intensity of at least 50 W/l into the liquid phase.

The process of the present invention makes it possible to perform the hydrogenation of phthalic anhydrides to the phthalides at low levels of catalyst, with a good space-time yield and in high selectivity.

Compared with the conventional processes for hydrogenating phthalic anhydride to phthalide with the aid of suspended Raney nickel, the process of this invention makes it possible to reduce the amount of Raney catalysts used appreciably for the same hydrogenation time, or to shorten the hydrogenation time dramatically for a comparable amount of Raney catalysts used.

The process of this invention surprisingly does not give rise to any deactivation of the Raney catalysts as arises with the conventional processes employing the customary mixing intensities in stirred or shaking autoclaves and which leads to long reaction times and correspondingly low space-time yields in such apparatus. In addition, the caking of the Raney catalysts which occurs in the conventional processes and which makes it difficult to remove the Raney catalysts after the reaction does not take place in the process of this invention.

As we have further found, the deactivation of the Raney catalysts which occurs in the conventional processes is likely to be attributable to the acidic by-products formed during the hydrogenation of phthalic anhydride to phthalide, such as toluic acid and phthalic acid (formed from unconverted phthalic anhydride and water of reaction), which combine with the Raney metals to form sparingly soluble salts which in turn are preferentially deposited on the catalyst surface. The introduction in the process of this invention of very high mixing intensities of at least 50 W/l gives rise to high shearing forces which are responsible for the continual removal of surface coatings of sparingly soluble metal salts such as nickel salts from the suspended Raney catalyst particles, so that the catalyst surface remains active throughout the entire reaction (cf. P.H.M.R. Cramers et al, Process Intensification with Buss Loop Reactors, in Proceedings of the Conference "Catalysis in Multiphase Reactors", Lyons, Dec. 7–9, 1994).

It is an essential feature of the process of this invention that the mixing apparatus which, in the hydrogenation, both mixes the gas and liquid phases and maintains the catalysts in suspended form introduces particularly high mixing intensities into the liquid phase, viz. at least 50 W/l of liquid phase, preferably from 50 to 2000 W/l of liquid phase, especially from 100 to 500 W/l of liquid phase.

This method of working gives rise to the above-recited advantages over the conventional hydrogenation processes which employ typical mixing intensities from 0.1 to 10 W/l of liquid phase as available for example from stirred reactors or shaking autoclaves.

The process of this invention can be carried out using any arrangement of hydrogenation apparatus which allows the introduction of at least 50 W/l via appropriate mixing apparatus. The process of this invention is advantageously carried out in a loop reactor in which a recirculating pump recirculates the liquid phase out of the reactor and feeds it back at the top of the reactor. The liquid phase may be fed back in, for example, by spraying it in finely divided form into the gaseous hydrogen atmosphere of the reactor, in which case the mixing intensity stipulated by this invention may be transferred to the liquid phase not only in the region of the recirculating pump but also in the region of the spray nozzle. The hydrogenation of this invention is carried out with particular advantage in a loop reactor comprising a gas and liquid recirculation system coupled via a multistream ejector mixing nozzle. For example, the process is advantageously carried out in a loop reactor plant having the following features:

1: reactor
2: recirculating pump
3: heat exchanger for liquid phase
4: multistream ejector mixing nozzle
5: recirculating line for liquid phase
6: feed line for hydrogen
7: discharge line for gas phase
8: feed and discharge line for liquid phase
9: optionally heated reactor wall
   a) liquid phase
   b) gas phase.

The loop reactor plant introduces suitably high mixing intensities especially in the region of the recirculating pump 2, via which an intensity of up to about 100 W/l can be introduced into the recirculated liquid phase, and in the region of the multistream ejector mixing nozzle 4, via which an intensity of from 200 to 800 W/l, locally up to 10,000 W/l, can be introduced.

The mixing intensity introduced using the mixing apparatus of the hydrogenation is conveniently determined in the manner described in Ind. Eng. Chem. Res. 1992, 31, 949–958.

The catalytic hydrogenation is generally carried out at temperatures from 50 to 400° C., preferably from 100 to 250° C., especially from 140 to 220° C., and at pressures from 1 to 400 bar, preferably from 5 to 300 bar, especially from 5 to 200 bar, particularly advantageously from 30 to 120 bar.

The hydrogenation catalysts used for the process of this invention are Raney catalysts. Suitable Raney catalyts are Raney nickel, Raney iron, Raney cobalt, Raney copper, preferably Raney nickel.

The Raney catalysts may be doped with suitable metals to increase the activity. It may be advantageous, for example, to use Raney nickel catalysts doped with metals of the 1st transition group of the periodic table, generally silver, copper, preferably copper", with metals of the 6th transition group of the periodic table, generally chromium, molybdenum or tungsten, preferably molybdenum, and/or with metals of the 7th group of the periodic table, generally manganese, rhenium, preferably rhenium. In general, the level of doping metals in the Raney nickel catalysts ranges from 0.01 to 10% by weight, preferably 0.1 to 5% by weight, based on the nickel present in the catalysts.

The Raney catalysts used according to this invention are prepared in a conventional manner. Raney nickel is obtained, for example, by alloying nickel and alkali-leachable substances, preferably aluminum and/or silicon, and subsequently leaching the alkali-soluble substances out using an alkali, such as aqueous sodium hydroxide solution.

The hydrogenation can be carried out without solvent, in which case the phthalic anhydride is used in molten form.

In general, the hydrogenation is carried out using a solvent. Examples of suitable solvents are ethers such as tetrahydrofuran, dioxane, glycol ethers, esters such as methyl acetate and methyl benzoate, lactones such as butyrolactone or phthalide, preferably the phthalide formed in the course of the hydrogenation, alcohols such as methanol, ethanol, propanol, butanol, hydrocarbons or mixtures thereof.

The weight ratio of phthalic anhydride to be hydrogenated to the solvent used is generally within the range from 1000:1 to 1:1000, preferably within the range from 500:1 to 1:500, especially within the range from 200:1 to 1:200.

The reaction of this invention is advantageously discontinued as soon as all the phthalic anhydride used has been hydrogenated. The time for discontinuation is determined for example by determining the phthalic anhydride still present, for example by gas chromatography or from the time course of hydrogen consumption.

The reaction product is worked up in a conventional manner, preferably by distillation.

In the compounds I and II, $R^1$, $R^2$, $R^3$ and $R^4$ are independently hydrogen; $C_1$–$C_4$-alkyl such as methyl, ethyl, n-propyl, isopropyl, n-butyl, isobutyl, sec-butyl, tert-butyl, preferably methyl and is ethyl, especially methyl; $C_1$–$C_4$-alkoxy such as methoxy, ethoxy, n-propoxy, isopropoxy, n-butoxy, isobutoxy, sec-butoxy, tert-butoxy, preferably methoxy and ethoxy, especially methoxy. $R^1$, $R^2$, $R^3$ and $R^4$ are particularly preferably all hydrogen.

The phthalic anhydrides II used as starting materials are well known, such as phthalic anhydride itself, or are obtainable by known processes (J. of Org. Chemistry 51, 3439–3446 (1986); Synthesis 223–224 (1985)).

The phthalides I are useful for example as starting materials for the synthesis of crop protection agents.

The Examples which follow illustrate the invention.

INVENTIVE EXAMPLE 1

A 70 l loop reactor is charged with 39.5 kg of phthalide as solvent, 16.9 kg of phthalic anhydride (PA) and 169 g Raney nickel (B 113 W from Degussa), which is suspended in butyrolactone, at 130° C. in the form of a melt. The reactor contents are recirculated at 5 m³/h. The mixing intensity introduced into the liquid phase is 100 W/l in the region of the recirculating pump and 1000 W/l in the region of the multistream ejector mixing nozzle. Hydrogen is injected to a pressure of 40 bar and the reactor contents are heated to 170° C. over 20 min. The hydrogenation is carried out 40 bar and 170° C. to constant pressure. Hydrogen uptake is 5700 standard l. The hydrogenation time is 102 min.

The product obtained is a colorless melt of the composition pressure. Hydrogen uptake is 5700 standard l. The hydrogenation time is 102 min.

The product obtained is a colorless melt of the composition

Phthalide 94.1% by weight
Water 4.0% by weight
PA 0.3% by weight
Toluic acid 1.4% by weight.

This corresponds to a PA conversion of 99% coupled with a selectivity of 93%.

COMPARATIVE EXAMPLE 2

A 0.5 l stirred autoclave equipped with a sparging stirrer is charged with 88.8 g of phthalic anhydride (PA), 207.2 g of phthalide and 0.90 g of Raney nickel (B 113 W from Degussa) in the form of a melt at about 120° C. After the stirrer has been switched on, hydrogen is injected to a pressure of 40 bar and the reactor contents are heated to 180° C. The hydrogenation is continued at this pressure and this temperature to constant pressure, while the contents are stirred at a speed of 500 or 1000 rpm. The experimental conditions and the results of the hydrogenation are summarized in the following table:

| Run No. | Speed rpm | Hydrogenation time min | Conversion % | Selectivity % | Hydrogen uptake standard l |
|---|---|---|---|---|---|
| 2a | 500 | 235 | 99.9 | 85 | 25.1 |
| 2b | 1000 | 225 | 99.7 | 83 | 24.8 |

Composition of products in % by weight

| Run No. | Phthalide | Water | PA | Toluic acid |
|---|---|---|---|---|
| 2a | 92.3 | 3.3 | <0.1 | 3.2 |
| 2b | 91.9 | 3.4 | 0.1 | 3.7 |

The present comparative example requires significantly longer hydrogenation times than Inventive Example 1 to achieve, what is more, distinctly lower selectivities.

INVENTIVE EXAMPLE 3

| Run No. | Concentration of PA based on PA + phthalide % by weight | Catalyst quantity g | Catalyst quantity % by weight, based on PA | Hydrogen uptake standard l | Hydrogenation time min | Conversion % | Selectivity % |
|---|---|---|---|---|---|---|---|
| 3a | 30 | 43 | 0.25[1] | 5800 | 160 | 99 | 88 |
| 3b | 30 | 54 | 0.35[2] | 5200 | 144 | 99 | 88.5 |
| 3c | 50 | 210 | 0.75[2] | 9700 | 65 | 100 | 88.6 |

[1] butyrolactone-moist
[2] water-moist

COMPARATIVE EXAMPLE 4

A 2 l autoclave equipped with a lift stirrer is charged with 413 g of phthalic anhydride (PA), 964 g of phthalide (688.5 g of PA and 688.5 g of phthalide for 4c) and the amount of Raney nickel reported in the table, as a melt. After inertizing with nitrogen and replacing with hydrogen, the reactor contents are heated to the reported temperature at a lift count of 160 per minute and the reported hydrogen pressure is injected. Hydrogenation is continued under these conditions to constant pressure.

The experimental conditions and the results are summarized in the following table:

| Run No. | Temperature °C. | Pressure bar | Catalyst quantity g | % by weight, based on PA | Hydrogen uptake standard 1 | Hydrogenation time min | Conversion % | Selectivity % |
|---|---|---|---|---|---|---|---|---|
| 4a | 170 | 40 | 4.13 | 1.0[1) | 136 | 365 | 100 | 75 |
| 4b | 183 | 80 | 1.03 | 0.25[1) | 137 | 1162 | 100 | 79 |
| 4c | 183 | 80 | 1.45 | 0.35[1) | 137 | 435 | 100 | 85 |
| 4d | 183 | 80 | 5.16 | 0.75[2) | 208 | 164 | 99 | 87 |

[1)]butyrolactone-moist
[2)]water-moist

The present comparative example requires signficantly longer hydrogenation times than Inventive Example 3.

We claim:

1. A process for preparing phthalides of the general formula I,

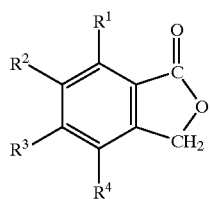

where $R^1$, $R^2$, $R^3$ and $R^4$ are independently hydrogen, $C_1$–$C_4$-alkyl or $C_1$–$C_4$-alkoxy, by hydrogenating phthalic anhydrides of the general formula II,

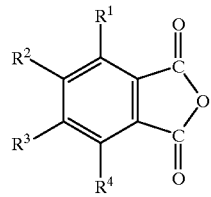

where $R^1$, $R^2$, $R^3$ and $R^4$ are each as defined above, with hydrogen in the presence of suspended catalysts of the Raney type in a hydrogenation apparatus by using a mixing apparatus to mix a liquid phase, which includes the catalyst and the phthalic anhydride used and resulting phthalide, and a gas phase, which includes the hydrogenating hydrogen, which comprises using the mixing apparatus to introduce a mixing intensity of at least 50 W/l into the liquid phase.

2. The process of claim 1, wherein the mixing intensity introduced is within the range from 50 to 10,000 W/l.

3. The process of claim 1, wherein the hydrogenation is carried out in a loop reactor comprising a gas and liquid recirculation system coupled via a multistream ejector mixing nozzle.

4. The process of claim 1, wherein the Raney catalysts are Raney nickel, Raney cobalt or Raney copper.

5. The process of claim 4, wherein the Raney catalyst is Raney nickel.

* * * * *